(12) United States Patent
Onishi et al.

(10) Patent No.: US 6,632,206 B1
(45) Date of Patent: Oct. 14, 2003

(54) DISPOSABLE DIAPER

(75) Inventors: Kazuaki Onishi, Kagawa-ken (JP);
Norihiko Ishikawa, Kagawa-ken (JP);
Yoko Yabe, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 4 days.

(21) Appl. No.: 09/666,584

(22) Filed: Sep. 21, 2000

(30) Foreign Application Priority Data

Sep. 21, 1999 (JP) .......................................... 11-267692

(51) Int. Cl.$^7$ ................................................ A61F 13/15
(52) U.S. Cl. ............................ 604/385.01; 604/385.17; 604/379
(58) Field of Search ................................. 604/379, 380, 604/385.01, 385.17

(56) References Cited

U.S. PATENT DOCUMENTS

| 4,585,448 A | * | 4/1986 | Enloe ......................... 604/378 |
| 4,631,062 A | * | 12/1986 | Lassen et al. ................. 604/385 |
| 4,685,915 A | * | 8/1987 | Hasse et al. .................. 604/378 |
| 4,828,555 A | * | 5/1989 | hermansson .................. 604/379 |
| 5,545,156 A | * | 8/1996 | DiPalma et al. ........... 604/385.1 |
| 5,554,142 A | | 9/1996 | Dreier et al. |
| 5,591,148 A | * | 1/1997 | McFall et al. ................ 604/378 |
| 5,688,259 A | * | 11/1997 | Osborn, III et al. ...... 604/385.1 |

FOREIGN PATENT DOCUMENTS

| GB | 588689 A | 5/1947 |
| JP | U-7-7620 | 2/1995 |

* cited by examiner

Primary Examiner—Weilun Lo
Assistant Examiner—Jacqueline F Stephens
(74) Attorney, Agent, or Firm—Butzel Long

(57) ABSTRACT

A disposable diaper is locally formed with a protuberance in a transversely middle zone of the diaper between urethral meatus and anus of a diaper wearer, and the diaper thus formed is capable of preventing loose passage discharged thereon form flowing toward the front side of the wearer.

7 Claims, 3 Drawing Sheets

DISPOSABLE DIAPER

BACKGROUND OF THE INVENTION

This invention relates to a disposable diaper for absorption and containment of excretion.

Most conventional disposable diapers are designed to rapidly absorb excretion and to contain their reliably by curving their substantially inner surface so that the inner surface may be placed against the wearer's crotch region around the urethral meatus and the anus. However, loose passage, if it is discharged on the diaper, may flow toward the belly side of the wearer before being absorbed and consequently cling to the wearer's crotch region particularly around the urethral meatus. Such a situation is often experienced by babies normally discharging loose passage.

Japanese Utility Model Application Disclosure No. 1995-7620 describes a disposable diaper in which the inner surface is formed with an annular projection adapted to be placed against the wearer's skin around the anus and a sink for loose passage is defined inside this annular projection serving to prevent loose passage from flowing in the undesirable manner as has been described above. In this way, this known diaper alleviates the possibility that loose passage might cling to the wearer's skin on the belly side before loose passage is absorbed by the diaper.

Loose passage clinging to the wearer's skin around the urethral meatus which often occurred in the conventional diaper prior to the Japanese Utility Model Application Disclosure No. 1995-7620 was unsanitary and took much time to wipe off and dispose of. Such operation of wiping off and putting away was troublesome particularly when urine and feces were discharged at once.

While the diaper disclosed in the aforesaid Application can overcome such a problem, a restriction is imposed in that the annular projection must be held in close contact with the wearer's body around the anus during use of the diaper. In addition, the annular projection is uncomfortably pressed against the wearer's skin when the wearer lies on his or her back and, as a result, a feeling of discomfort due to the diaper put on may be further emphasized.

SUMMARY OF THE INVENTION

To solve the aforesaid problem, an object of this invention is to provide a disposable diaper that is capable of being easily put on the wearer and to prevents loose passage from flowing toward the front side of the wearer by an arrangement which is not discomforting to the wearer.

According to this invention, there is provided a disposable diaper having a transverse direction and a longitudinal direction comprising: a liquid-pervious topsheet; a liquid-impervious backsheet; a liquid-absorbent core disposed between the topsheet and the backsheet; and the diaper being locally formed on an inner surface thereof with a protuberance lying in a transversely middle zone of the diaper between urethral meatus and anus of the wearer. It is preferable that the protuberance is elastically deformable as it comes in contact with the wearer's skin.

The disposable diaper according to this invention is provided between the urethral meatus and the anus of the wearer with the protuberance configured to prevent undesirable situations such as flow of loose passage toward the front side of the wearer, flow of urine toward the rear side of the wearer and mixing loose passage with urine. Such protuberance is capable of fulfilling its function even when it is not in close contact with the wearer's crotch so far as it lies between the urethral meatus and the anus. Additionally, the diaper can be easily put on the wearer's body because no particular care is necessary for this diaper to position the protuberance when the diaper is being put on the wearer. Furthermore, the protuberance gives the wearer no irritation even when the wearer lies on his or her back.

DETAILED DESCRIPTION OF THE PREFERRED EMBODIMENTS

Details of this invention will be more fully understood from the description given hereunder with reference to the accompanying drawings.

Figure 1:
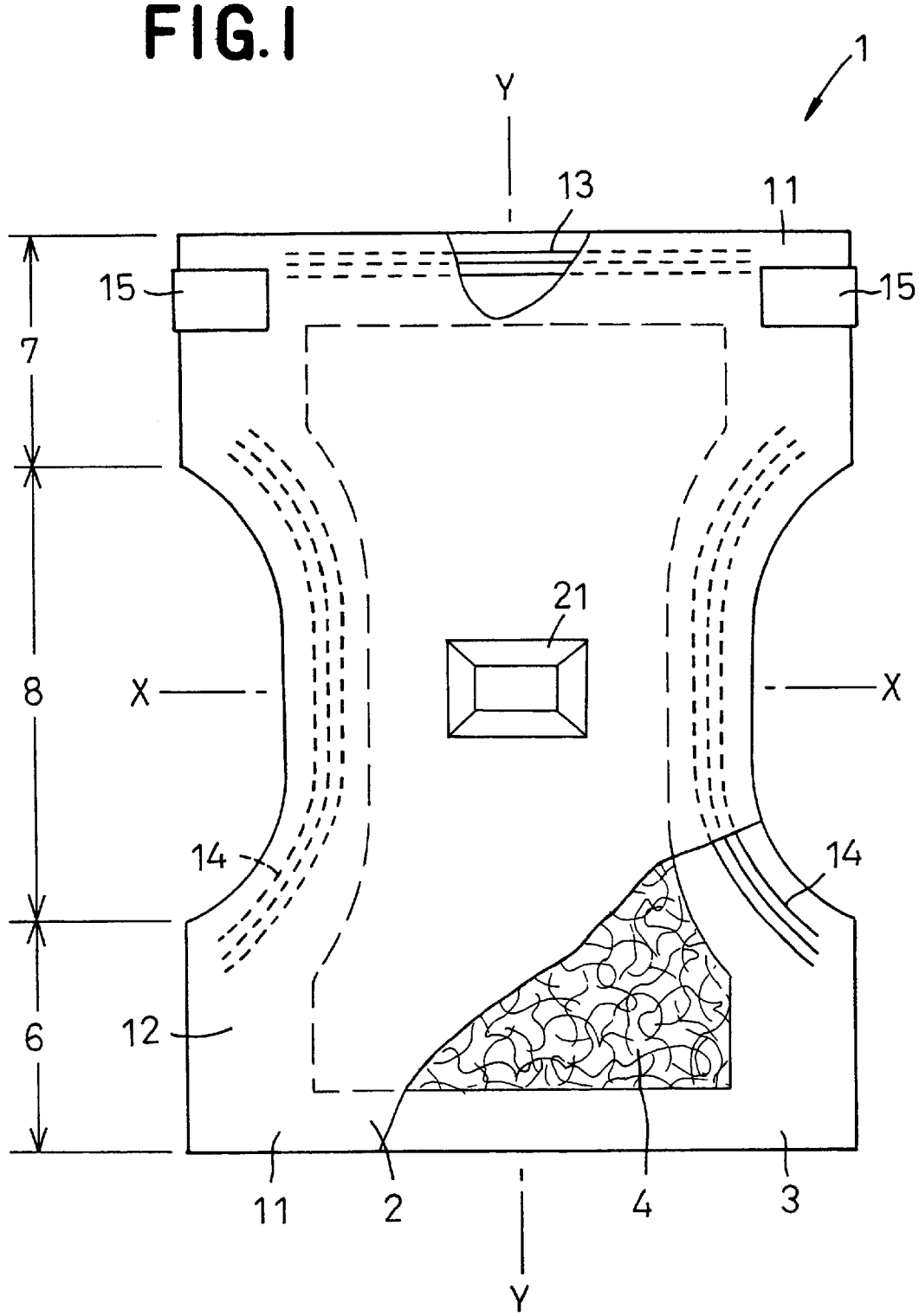
FIG. 1 is a plan view depicting one embodiment of a partially cutaway disposable diaper according to this invention.

A disposable diaper 1 depicted by FIG. 1 in a plan view comprises a liquid-pervious topsheet 2, a liquid-impervious backsheet 3 and a liquid-absorbent core 4 disposed between these two sheets 2, 3. The diaper 1 has center line Y—Y transversely bisecting the diaper 1 and center line X—X longitudinally bisecting the diaper 1. The topsheet 2 and the backsheet 3 extend outward beyond a peripheral edge of the core 4 and put flat together at these extensions to form a pair of end flaps 11, 11 transversely extending in parallel to each other and a pair of side flaps 12, 12 longitudinally extending in parallel to each other. The diaper 1 is composed, in its longitudinal direction, of a front waist region 6, a rear waist region 7 and a crotch region 8 extending between these two waist regions 6, 7. Transversely opposite side edges of the crotch region 8 are curved inwardly of the diaper 1. The end flap 11 on the rear waist region 7 and the pair of side flaps 12, 12 are provided with an elastic member 13 intended to be associated with a waist-opening and elastic members 14, 14 intended to be associated with leg-openings, respectively. These elastic members 13, 14 are disposed between the topsheet 2 and the backsheet 3 and secured by means of hot melt adhesive (not shown) to the inner surface of at least one of these two sheets 2, 3. In the rear waist region 7, the pair of side flaps 12, 12 are provided with tape fasteners 15, 15, respectively.

The diaper 1 is formed in a transversely middle zone, preferably on the centerline Y—Y with a protuberance 21. This protuberance 21 is positioned longitudinally of the diaper 1 so that the protuberance 21 may lie between urethral meatus and anus of the wearer as the diaper 1 is put on the wearer's body. FIG. 1 exemplarily illustrates this protuberance 21 lying on the center line X—X.

Figure 2:
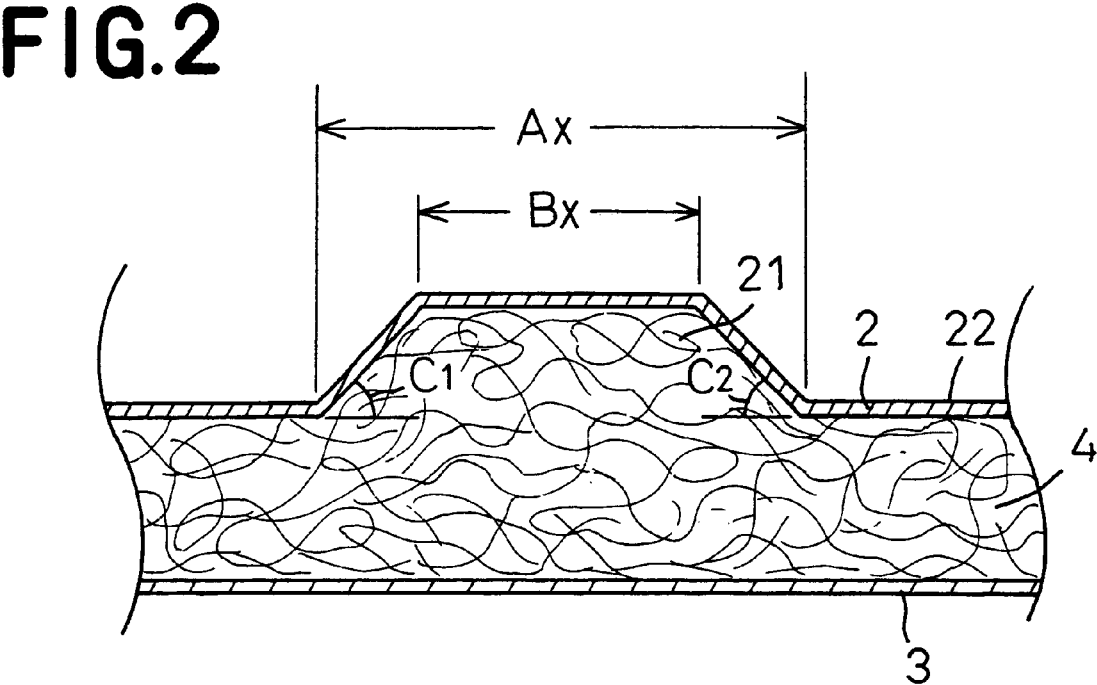
FIG. 2 is a fragmentary sectional view taken along line X—X in FIG. 1.
Figure 3:
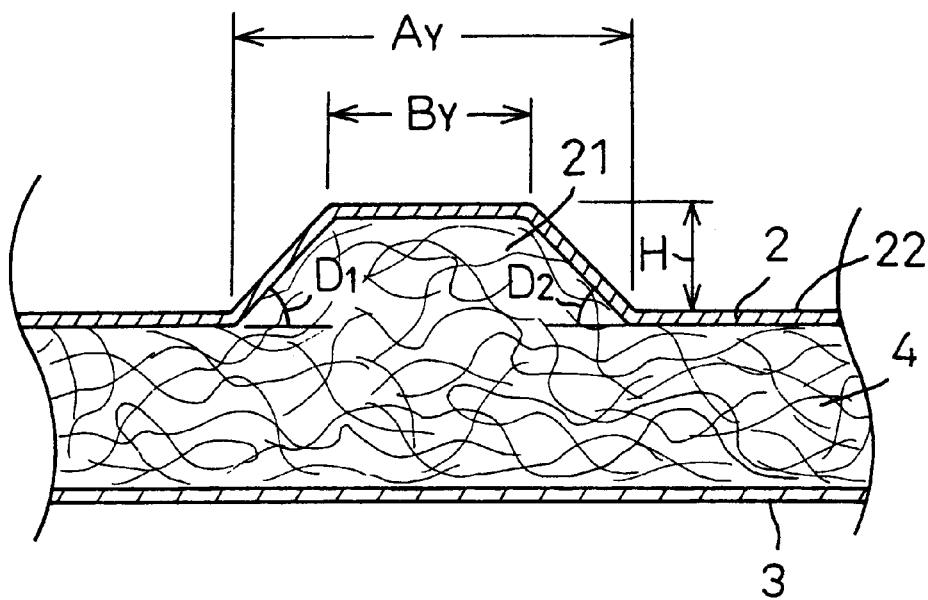
FIG. 3 is a fragmentary sectional view taken along line Y—Y in FIG. 1.

FIGS. 2 and 3 are sectional views taken along lines X—X and Y—Y, respectively, in FIG. 1. In the case of the protuberance 21 having a trapezoidal cross-section as shown, depending on a size of the diaper 1, a height H as measured from a flat inner surface 22 of the diaper 1 is 10~100 mm, a length $A_X$ of the base side as measured in the direction X—X is 10~100 mm and a length $A_Y$ of the base side as measured in the direction of Y—Y is 10~80 mm. Lengths $B_X$, $B_Y$ of the top sides as measured in the directions X—X and Y—Y, respectively, are 5~80% of the lengths of the corresponding base sides. More preferably, the lengths $B_X$, $B_Y$ of the respective top sides are at least 5 mm and 20~80% of the lengths $A_X$, $A_Y$ so that the top of the trapezoid should not be acute. The lengths $A_X$, $A_Y$ of the respective base sides may be equal to each other or the length $A_X$ may be larger than the length $A_Y$. Similarly, the lengths $B_X$, $B_Y$ of the respective top sides may be equal to each other or the length $B_X$ may be larger than the length $B_Y$. Respective oblique sides of the protuberance 21 intersect the flat inner surface 22 at angles $C_1$, $C_2$, $D_1$, $D_2$. The angle $C_1$ is equal to the angle $C_2$. Referring to FIG. 3, the angles $D_1$, $D_2$ appearing in the front and rear waist regions 6, 7, respectively, may be equal to or different from each other. The protuberance 21 formed in this manner easily comes in close contact with the wearer's crotch from below.

The protuberance 21 as illustrated can be obtained by forming the core 4 so as to protrude locally and then covering the upper surface of the core 4 thus formed with the liquid-pervious topsheet 2. If desired, the upper surface of the core 21 including the protuberance 21 may be intermittently joined to the topsheet 2 by means of hot melt adhesive. While not specified, the core 4 may be obtained by compressing fluff pulp or a mixture of fluff pulp and highly water absorptive grains into a desired shape.

With the diaper 1 having such protuberance 21, the latter serves as a partition rising on the flat inner surface 22 adapted to separate the urethral meatus and the anus in the longitudinal direction. The protuberance 21 thereby prevents urine from flowing toward the rear side of the wearer and prevents loose passage from flowing toward the front side of the wearer. The preventive effect of the protuberance 21 can be obtained even when the protuberance 21 is not in close-contact with the wearer's crotch and is significant when the protuberance 21 is in close contact with the wearer's crotch.

Figure 4:
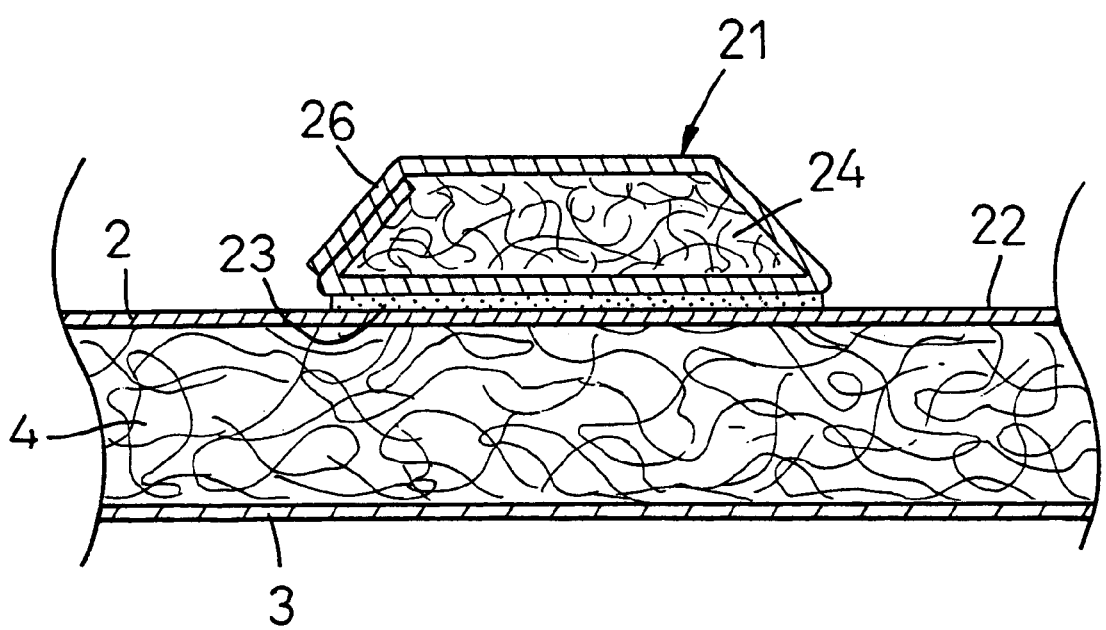
FIG. 4 is a view similar to FIG. 2 but depicting another embodiment of this invention.

FIG. 4 is a view similar to FIG. 2 but showing an alternative embodiment of this invention. In the case of this alternative embodiment, the protuberance 21 is separately prepared and joined to the flat inner surface 22 by means of adhesive 23. The protuberance 21 comprises a core material 24 having a trapezoidal cross-section and a covering sheet 26. The core material 24 is elastic and formed by a spongy material or a fibrous assembly adapted to be elastically deformable both in vertical and lateral directions as viewed in FIG. 4 as it comes in contact with the wearer's skin. An elastic deformability of the core material 24 is preferably of a degree at which its thickness is reduced by in the order of 10~80% under a pressure of 10 gf/cm² exerted on the core material 24. To obtain such a degree of elasticity, suitable crimped conjugated fiber may be used as component fiber of the fibrous assembly. The covering sheet 26 serves to hold a desired shape of the core material 24 and to improve external appearance as well as a touch of the protuberance 21. The covering sheet 26 may be hydrophilic or hydrophobic. It is possible to use the core material 24 as well as the covering sheet 26 of hydrophilic nature so that the protuberance 21 may have a body fluid absorptivity and inversely it is also possible to use the core material 24 as well as the covering sheet 26 of hydrophobic or water-repellent nature so that the protuberance 21 may resist absorption of urine and loose passage.

While the protuberance 21 has been described and illustrated as having the trapezoidal cross-section, it is also possible without departing from the spirit and the scope of this invention, to use an alternatively shaped protuberance 21 such as the semispherical or semicylindrical protuberance 21.

What is claimed is:

1. A disposable diaper having a transverse direction and a longitudinal direction comprising:

a liquid-permeable topsheet;

a liquid-impervious backsheet;

a liquid-absorbent core disposed between said top sheet and backsheet; and said diaper being locally formed on an inner surface thereof with a protuberance located exclusively in a transversely middle zone of said diaper, which transversely middle zone is spaced inwardly from both transversely opposite edges and longitudinally opposite ends of said absorbent core, so that the protuberance is positioned between a urethral meatus and anus of a wearer of the diaper, said protuberance comprising a liquid-absorbent material and a liquid-permeable sheet covering an upper surface of said liquid-absorbent material, said protuberance integrally extending along the inner surface of said diaper and having a transverse dimension that extends in the transverse direction of the disposable diaper and a longitudinal dimension that extends in the longitudinal direction of the diaper, said transverse dimension being greater than said longitudinal dimension.

2. A disposable diaper according to claim 1, wherein said protuberance is elastically deformable.

3. A disposable diaper according to claim 1, wherein said protuberance has a height of about 10 mm to about 100 mm as measured from said inner surface of the diaper.

4. A disposable diaper according to claim 1, wherein said protuberance has a trapezoidal cross-section along at least one of said transverse direction and longitudinal direction.

5. A disposable diaper according to claim 4, wherein said protuberance has a trapezoidal cross-section in which base sides extending in said transverse direction and longitudinal direction are dimensioned to be about 10 mm to about 100 mm and about 10 mm to about 80 mm, respectively, and top sides thereof are dimensioned to be about 5% to about 80% of the dimensions of the corresponding base sides.

6. A disposable diaper according to claim 1, wherein said protuberance is formed by protruding a portion of said liquid-absorbent core upwardly and covering the protruded portion with said topsheet.

7. A disposable diaper according to claim 1, wherein said protuberance comprises a liquid-absorbent material prepared separately from said liquid-absorbent core and a liquid-permeable sheet covering an entire surface of said liquid-absorbent material, a portion of said liquid-permeable sheet being positioned at a bottom of said liquid-absorbent material is, integrally joined to the topsheet.

* * * * *